United States Patent [19]
Tafesh et al.

[11] Patent Number: 5,399,764
[45] Date of Patent: Mar. 21, 1995

[54] PROCESS FOR PREPARING ARYLKETOAMINES

[75] Inventors: Ahmed M. Tafesh; George Kvakovszky, both of Corpus Christi; Charlet R. Lindley, Portland, all of Tex.

[73] Assignee: Hoechst Celanese Corporation, Somerville, N.J.

[21] Appl. No.: 246,892

[22] Filed: May 20, 1994

Related U.S. Application Data

[62] Division of Ser. No. 191,849, Feb. 4, 1994, Pat. No. 5,349,090.

[51] Int. Cl.[6] .................. C07C 209/52; C07C 225/10
[52] U.S. Cl. ..................................... 564/343; 564/337
[58] Field of Search ................... 564/337, 343

[56] References Cited

U.S. PATENT DOCUMENTS

| | | | |
|---|---|---|---|
| 1,995,709 | 9/1931 | Hartung | 260/128.5 |
| 2,505,645 | 4/1950 | McPhee | 260/570.6 |
| 2,567,906 | 9/1951 | Hartung | 260/570.6 |
| 2,784,228 | 3/1957 | Hartung | 260/570.6 |
| 3,028,929 | 4/1962 | Wilbert et al. | 260/570.6 |
| 3,966,813 | 6/1976 | Satzinger et al. | 260/570.6 |
| 5,124,489 | 6/1992 | Durrwachter et al. | 568/630 |
| 5,198,585 | 3/1993 | Tafesh et al. | 564/343 |

*Primary Examiner*—Peter O'Sullivan
*Attorney, Agent, or Firm*—James J. Mullen; Doanld R. Cassady

[57] ABSTRACT

Arylketoamines are prepared by reacting arylisonitrosoalkanones with hydrogen in the presence of a transition metal catalyst and a liquid carboxylic acid at a temperature of less than about 60° C.

9 Claims, No Drawings

PROCESS FOR PREPARING ARYLKETOAMINES

This is a divisional of application Ser. No. 08/191,849, now U.S. Pat. No. 5,349,090.

BACKGROUND OF THE INVENTION

FIELD OF THE INVENTION

The present invention relates to methods for the preparation of substituted or unsubstituted arylketoamines from substituted or unsubstimted arylisonitrosoalkanones.

Substituted and unsubstituted arylketoamines are chemical intermediates of great importance by virtue of their relationship to ephedrine and ephedrine-like substances. For example, the derivative p-hydroxyphenylethanolamine (octopamine) is a sympathomimetic which produces vasoconstricting and cardiotonic effects.

RELATED APPLICATIONS

The present patent application is commonly owned by the same Assignee as the following cases:
Ser. No. 08/106,030 filed Aug. 13, 1993, entitled, "Process for Preparing Substituted and Unsubstituted Phenylglyoxals from Corresponding Substituted and Unsubstituted Acetophenones".

DESCRIPTION OF RELATED ART

The following prior an references are disclosed in accordance with the terms of 37 CFR 1.56, 1.97, and 1.98.

U.S. Pat. No. 1,995,709 discloses the preparation of substituted phenylpropanolamines.

U.S. Pat. No. 2,567,906 discloses the preparation of 1-(p-aminophenyl)-2-amino-1-propanol.

U.S. Pat. No. 2,505,645 discloses the preparation of α-phenyl-B-hydroxyphenyl-B-hydroxyethylamine.

U.S. Pat. No. 2,784,228 discloses the preparation of amino alcohols by the catalytic reduction of α-oximino ketones.

U.S. Pat. No. 3,028,429 discloses the preparation of 1-phenyl-2-aminopropanol by the hydrogenation of isonitrosopropiophenone.

U.S. Pat. No. 3,966,813 discloses the preparation of 1-(hydroxyphenyl)-2-aminoethanol.

U.S. Pat. No. 5,124,489 discloses the preparation of substituted phenethanol ethers by the catalytic reduction of the corresponding substituted phenylglyoxal acetals.

U.S. Pat. No. 5,198,585 discloses the preparation of acid addition salts of arylketoamines.

All of the above-cited prior an references, including any others disclosed herein, are incorporated herein by reference in their entirety.

All of the above-cited prior an references have one thing in common; the yields of the desired end products, i.e., the arylketoamines, such as the amino-hydroxyacetophenone (AHAP), are low. Thus, there is always a need in commercial processes to improve the yield and consequently reduce production costs and unwanted by-products.

SUMMARY OF THE INVENTION

In accordance with the present invent,on, a method for the preparation of an arylketoamine is disclosed, the method comprising the steps of:

a) providing an arylisonitrosoalkanone compound of the formula:

wherein
$R_1$ = an hydroxyl or $C_1$-$C_8$ alkyloxy radical,
$R_2$ = hydrogen or a $C_1$-$C_8$ alkyl or cycloalkyl radical, and
Ar = a substituted or unsubstituted phenyl radical, or a naphthyl radical unsubstituted or substituted wherein one or more substituents are selected from the group consisting of hydroxyl, alkoxy, alkyl, phenyl, and benzyl radicals, wherein the alkyl component is a branched or unbranched $C_1$-$C_8$ alkyl radical, wherein any alkyl, phenyl and benzyl radicals are optionally substituted with one or more substituents selected from hydroxyl, sulfonic acid, and sulfonic acid radicals, and wherein said phenyl and benzyl substituents are optionally substituted with a $C_1$-$C_8$ alkyl or $C_1$-$C_8$ alkoxy radical, or both; and b) reacting said isonitrosoalkanone compound with hydrogen in a reaction medium consisting essentially of a liquid carboxylic acid in the presence of transition metal catalyst to produce a reaction product comprising, as its major component, the arylketoamine.

In the method of this invention hydrogen is provided in sufficient quantity for reaction of 2 mole equivalents of hydrogen in the conversion of the arylisonitrosoalkanones to an arylketoamine. Thus, stoichiometrically, the reaction may be depicted as:

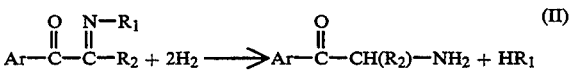

where Ar, $R_1$, and $R_2$ have the same meaning as above. The critical feature of the present invention is the use of a liquid carboxylic acid at a defined temperature range to conduct the hydrogenation to form the arylketoamine.

The transition metal catalyst is supported on an inert support, and suitably is provided in an amount of from about 0.005% to about 1.5% by weight based on the amount of the arylisonitrosoalkanone compound. The transition metal is selected from the group consisting of platinum, palladium, nickel, rhodium, and combinations thereof, and preferably is palladium on a carbon support. The reaction is carried out under hydrogen pressure ranging from about 1.0 psi to about 300 psi, and at a critical temperature less than 60° C., preferably ranging from 10° C. to about 35° C.

In accordance with another facet of this invention, arylketoamines can be prepared from substituted or unsubstituted arylalkanones.

The arylalkanone is reacted with a source of a nitrosonium ion (such as nitrosyl chloride or a compound of the formula $NO^+X^-$ wherein x is halogen, sulfate, phosphate, nitrite, or acetate) in the presence of a strong acid to form the substituted or unsubstituted arylglyoxal/arylalkyl-α-diketone. The arylglyoxal/arylalkyl-α-diketone is then subjected to an oximation reaction to produce the arylisonitrosoalkanone.

DETAILED DESCRIPTION OF THE INVENTION

In accordance with the present invention, excellent yields of substituted and unsubstituted arylketoamines are obtained by hydrogenating arylisonitrosoalkanones in the presence of a supported transition metal catalyst in a reaction medium comprising a liquid carboxylic acid.

The substituted and unsubstituted arylisonitrosoalkanones employed in the invention have the formula:

in which $R_1$ represents a hydroxyl or hydrogen or $C_1$-$C_8$ alkyloxy radical and $R_2$ represents hydrogen or a $C_1$-$C_8$ alkyl or cycloalkyl radical, and Ar represents substituted or unsubstituted phenyl or naphthyl radical with one or more substituents selected from the group consisting of hydroxyl, alkoxy, alkyl, phenyl, benzyl, and aryloxy radicals, wherein the alkyl in the alkyl-containing substituent(s) is a branched or unbranched $C_1$-$C_8$ alkyl radical and any of such alkyl and the phenyl and benzyl radicals may be optionally substituted with one or more substituents selected from hydroxyl, sulfonic acid, and sulfinic acid radicals, the phenyl and benzyl substituents also or alternatively being optionally substituted with one or more $C_1$-$C_8$ alkyl or $C_1$-$C_8$ alkoxy, or both, radicals.

Hydrogenation of the substituted or unsubstituted arylisonitrosoalkanones is carried out using hydrogen in the presence of a transition metal hydrogenation catalyst selected from the group consisting of platinum, palladium, nickel, and rhodium or mixtures thereof on an inert support. The inert support typically comprises carbon or barium sulfate, and the hydrogenation catalyst comprises from about 1% by weight to about 25% by weight of the combination including hydrogenation catalyst and inert support. The preferred inert support material is carbon, and the most preferred hydrogenation catalyst comprises palladium on carbon, wherein the palladium comprises from about 5% by weight to about 25% by weight of the combination of palladium on carbon, as previously disclosed.

The hydrogenation is conducted under positive hydrogen pressures of from about 1.0 to about 300 psi, preferably in the range from about 5 to about 100 psi at temperatures less than 60° C., preferably from about 10° C. to about 35° C.

It has unexpectedly been found that at the above temperatures, i.e., less than 60° C., and with the use of a liquid carboxylic acid, the yields of the desired end products, i.e., the arylketoamines, are substantially high and are significantly improved over the prior art processes as exemplified by U.S. Pat. No. 5,198,585. The exact theory of what causes this significant increase in yields is not known. However, it is theorized that the liquid carboxylic acid acts or functions in a dual capacity, i.e., as a co-catalyst and as a solvent. The present Applicants do not desire to be limited by these theories.

As previously mentioned, the use of the liquid carboxylic acid and the lower temperatures are critical features of this invention.

The liquid carboxylic acid is any one which can substantially dissolve the particular arylisonitrosoalkanones therein and has a melting point of less than 60° C. Those carboxylic acids include, without limitation, formic, acetic, propanoic, butyric, valeric, caproic, heptanoic, octanoic, nonanoic, undecanoic, isobutyric, isovaleric, cyclohexane carboxylic acid, and mixtures thereof. It is also critical that the particular carboxylic acid be a saturated carboxylic acid, i.e., a straight chain saturated carboxylic acid, a branched chain saturated carboxylic acid, a substituted saturated carboxylic acid, and/or ring carboxylic acid. This carboxylic acid must not interfere with the hydrogenation reaction.

The liquid carboxylic acid, preferably acetic acid, comprises from about 50% by weight to about 95% by weight of the reaction medium, and more preferably from about 80% by weight to about 90% by weight of the reaction medium.

Typically the conversion of the arylisonitrosoalkanones of the formula disclosed above to an arylketoamine, using the method of the present invention, results in a yield above about 95% based on the arylisonitrosoalkanone.

More particularly, the substituted and unsubstituted arylketoamines are obtained by reacting about two molar equivalents of hydrogen, based on the quantity of arylisonitrosoalkanone, wherein the arylisonitrosoalkanone is present in a quantity ranging from about 5% by weight to about 50% by weight, preferably from about 5% by weight to about 30% by weight, of the reaction medium, and wherein the reaction is carried out in the presence of a transition metal on an inert substrate (typically carbon), wherein the overall catalyst composition comprises from about 0.5% by weight to about 25% by weight, preferably from about 1% by weight to 10% by weight of the transition metal, and wherein the catalyst is present in quantity sufficient to provide from about 0.005% by weight to about 5.0% by weight, preferably from about 0.01% by weight to about 1.5% by weight, of the transition metal based on weight of the arylisonitrosoalkanone.

In preferred embodiments, 1-(o- or p-hydroxyphenyl)-2-aminoethanone, i.e., α-amino-o- or p-hydroxyacetophenone (AHAP), is produced by the method of the present invention using o- or p-hydroxyisonitrosoacetophenone (HINAP) as the arylisonitrosoalkanones precursor. In order to produce 1-(o- or p-hydroxyphenyl)-2-aminoethanone, i.e., α-amino-o- or p-hydroxyacetophenone (AHAP), hydrogen is reacted in the presence of a palladium on carbon catalyst. The amount of hydrogen reacted is 2 molar equivalents based on moles of o- or p-hydroxyisonitrosoacetophenone. The hydrogen pressure in the reactor preferably ranges from about 1.0 psi to about 300 psi. The o- or p-hydroxyisonitrosoacetophenone is suitably present in an amount ranging from about 5% by weight to about 50% by weight of the reaction medium, preferably in an amount ranging from about 5% by weight to about 25% by weight of the reaction medium. The liquid carboxylic acid is suitably present in the reaction medium in an amount ranging from about 50% by weight to about 95% by weight of the reaction medium, preferably from about 80% by weight to about 90% by weight of the reaction medium. The palladium on carbon catalyst, which typically comprises about 5% by weight to about 10% by weight palladium, is present in an amount such that the palladium present ranges from about 0.005% by weight to about 1.5% by weight of the o- or p-hydroxyisonitrosoacetophenone. The arylketoamine of this invention and which is exemplified in this disclosure is the 1-(o- or p-hydroxyphenyl)-2-aminoethanone (α-amino-o- or p-hydroxyacetophenone (AHAP).

Examples of arylalkanones usable in the above-described process are those wherein the aryl of the arylalkanone is an unsubstituted phenyl or naphthyl radical or is a substituted phenyl or naphthyl radical having substitution of the kind previously described. Such arylalkanones include, but are not limited to, o- and p-hydroxyacetophenone, o-, and p-methylacetophenone, p-ethylacetophenone, p-propylacetophenone, p-butylacetophenone, o- and p-methoxyacetophenone, o- and p-ethoxyacetophenone, 2,4-methoxyacetophenone, p-phenylacetophenone, 2-methoxy-4-methylacetophenone, p-acetonaphthone, β-acetonaphthone, propiophenone, o- and p-methoxypropiophenone, p-methylpropiophenone, p-ethylpropiophenone, butyrophenone, p-methylbutyrophenone, p-methoxybutyrophenone, valerophenone and p-methylvalerophenone, p-acetamidopropiophenone, p-hydroxyphenylacetophenone (4-HAP), p-hydroxyphenylpropiophenone, 1-(4-methylphenyl)propiophenone, and p-phenylsulfonyl-acetophenone, 4,5 dihydroxy-1-indanone, 5,6-dihydroxy-1-indanone, 4,5 dimethoxy-1-indanone and 5,6-dimethoxy-1-indanone.

In a still further embodiment of the present invention wherein arylketoamines are prepared, such arylketoamines (such as AHAP) are prepared from substituted or unsubstituted arylglyoxals/arylalkyl-α-diketones which are first reacted with an amine compound such as $NH_2OH$ or their salts such as $NH_2OH \cdot HCl$ to form the substituted or unsubstituted arylisonitrosoalkanones, e.g., HINAP, which in turn is hydrogenated via the present invention process to form the arylketoamines. The above reactions are shown below in Scheme 1:

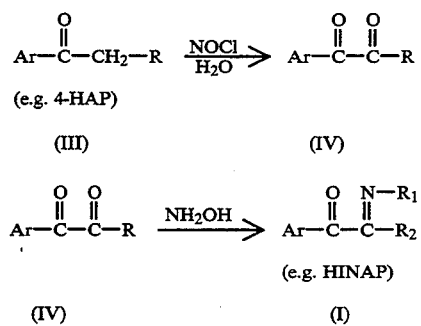

Thus, a substituted or an unsubstituted acetophenone of Formula III is converted to a substituted or unsubstituted phenylglyoxal of Formula IV, e.g. hydroxyphenyl glyoxal (HPGO). The substituted acetophenone, such as 4-hydroxyacetophenone (4-HAP), is reacted with a source of nitrosonium ion in the presence of water and in the presence of a strong mineral acid. Water is acting as either a reactant or a solvent, or both. It should be understood that, in this embodiment, Ar, which was previously defined, should be such that the compound of Formula III is sufficiently soluble in water to provide sufficient contact between the reactants for the reaction therebetween to proceed.

Once the phenylglyoxal is formed, it is then subjected to an oximation reaction and conditions to produce the arylisonitrosoalkanone. Suitable oximating agents include $NH_2OH$ and its salts. These type reactions are normally conducted in the liquid phase and thus require a suitable solvent such as water, alcohols, a dipolar aprotic solvent, and the like. The reaction generally proceeds at room temperature, i.e. about 20° C.

The following examples further illustrate the invention but are not to be construed as a limitation on the scope of the invention contemplated herein.

EXAMPLE 1 (COMPARATIVE)

This is a repeat of Example 1 of U.S. Pat. No. 5,198,5785. To a three-neck 2 L flask is added 2.2 moles of dry HCl to 1000 mL of dry dimethyl formamide (DMF). To the flask is then added 272 grams (2 moles) of p-hydroxyacetophenone all at once. The mixture is stirred until all solid dissolved. Then, 296 mL (2.2 moles) of 90% tertiary butyl nitrite (in tertiary butanol) is added very slowly to maintain the reaction medium temperature at about 40° C., which takes about two hours, after which the reaction medium is stirred for an additional three hours while maintaining the temperature at about 40°-45° C., and the reaction was left overnight at room temperature. A 200 mL sample is taken from the reaction mixture and was subjected to high vacuum (30° C., 28 inches water) whereupon water in the sample is evaporated and the reaction mixture is dry.

After filtration the crude but dry hydroxyisonitrosoacetophenone solution is added to a 1 L autoclave reactor, which is pressure checked, is charged with 12.5 g of 5% palladium on carbon and 178 mL of 4.2M HCl in dry DMF. The reactor is sealed then degasseal three times with nitrogen and three times with hydrogen. The reactor is then pressurized to 100 psi with hydrogen and stirred at 1200 rpm. The reaction heated itself to 27.6° C. The course of the reaction is tabularized.

| Time | Temp. (degrees C.) | Reactor Pressure (psig) | Surge Vessel Pressure (psig) |
|---|---|---|---|
| 11:00 | 25.5 | 102 | 436 |
| 11:30 | 26.8 | 102 | 434 |
| 12:30 | 27.6 | 102 | 420 |
| 13:40 | 27.4 | 102 | 406 |
| 14:05 | 27.6 | 98 | 403 |
| 15:00 | 26.6 | 98 | 320 |
| 15:20 | 26.7 | 98 | 386 |
| 16:00 | 27.2 | 98 | 382 |
| 21:00 | 26.2 | 98 | 315 |

The reaction mixture from the reactor is filtered and then concentrated under reduced pressure and the crude brown crystals are recrystallized from ethanol to give, after drying pure α-amino-p-hydroxyacetophenone (AHAP) in 70% yield.

EXAMPLE 2

Into a 300 ml autoclave (reactor) is charged 35.66 grams dry, recrystallized p-hydroxyisonitrosoacetophenone (HINAP) and 1.2 grams of 10% palladium on carbon catalyst followed by 119.94 grams of glacial acetic acid. The reactor is sealed and degassed three times with nitrogen and then pressure checked with nitrogen at 100 psi for ten minutes. The reactor is degassed three times with hydrogen and then pressurized to 80 psig. Stirring at 1200 rpm is initiated and there is a rapid exotherm. An ice bath is applied in order to maintain the temperature between 24° to 30° C. The reaction consumes 128 psi hydrogen (two equivalents as calculated by the ideal gas flow). The hydrogen feed is shut off and stirring is discontinued. The reactor is vented then degassed three times with nitrogen. The reaction slurry is vacuum filtered by a Buchner funnel yielding 15 270.7 grams of yellow solution. LC analyses of the solution results in the following:

|  | Octopamine.HCl | AHAP.HCl | HINAP | Unknown |
|---|---|---|---|---|
| Solution | 0.05 | 12.9 | 0.40 | 0.09 |
| Free base (%) | 0.04 | 10.4 | 0.40 | 0.09 |
| Weight, grams | 0.11 | 28.15 | 1.08 | 0.24 |
| Yield (%) | 0.40 | 102.90 | 3.60 | 0.90 |
| Yield % (adjusted) | 0.40 | 95.10 | 3.60 | 0.90 |

It can be seen from the above results that the yield of AHAP was 102.9% (95.1% by difference) based on HINAP. The conversion of HINAP was 96.4%. Compared to Example 1 above, the yields of AHAP (in Example 2) were quite unexpectedly high, i.e. 102.9% (95.1% adjusted) versus 70.0%, in practicing the novel process of the present invention. One of the key issues in practicing the present invention process is to facilitate high yields without over-hydrogenation to octopamine and/or tyramine which are undesirable by-products. As can be seen, the present invention accomplishes these objectives.

EXAMPLES 3 & 4

The process of Example 2 was repeated twice using the same procedure and starting materials. The results of these two repeats are shown below along with Example 2:

| Example | Yield % (based on HINAP) | | | | |
|---|---|---|---|---|---|
|  | Octopamine | AHAP | HINAP Conversion | HINAP | Unknown |
| 2 | 0.4 | 95.1 | 96.4 | 3.6 | 0.9 |
| 3 | 0.3 | 98.5 | 98.5 | 1.5 | — |
| 4 | 2.8 | 99.3 | 99.3 | 0.7 | — |

EXAMPLE 5 (COMPARATIVE)

In order to demonstrate a critical feature of the present invention, i.e., use of only the liquid carboxylic acid and in the absence of a dipolar aprotic solvent, the following example is conducted using a mixture of a liquid carboxylic acid and a dipolar aprotic solvent. Into a 300 ml autoclave (reactor) is charged 60.90 grams of washed p-hydroxyisonitrosoacetophenone (HINAP) (49.8%). The catalyst, 1.2347 grams of 10% palladium on carbon, is added to the autoclave followed by 100.03 grams of dimethyl formamide (DMF and 20.17 grams of glacial acetic acid. The reactor is sealed and degassed three times with nitrogen, then three times with hydrogen, and then is pressurized at 80 psi with hydrogen. Stirring at 1200 rpm is initiated and a modest exotherm develops. An ice bath is applied as needed to maintain the reaction between 26 to 30° C. The reaction consumes 155 psi hydrogen. The reaction rate is much slower than in Example 2 which uses only glacial acetic acid. After six hours, the reactor is opened and the reaction slurry is filtered on a Buchner funnel. The reactor is rinsed with 64.8 grams of DMF. The filtrate, 240.9 grams, is submitted for LC analyses as shown below:

|  | Octopamine.HCl | Tyramine.HCl | AHAP.HCl | HINAP | Unknown |
|---|---|---|---|---|---|
| Solution | 3.00 | 2.93 | 9.10 | 0.40 | 0.39 |
| Free Base (%) | 2.40 | 2.30 | 7.30 | 0.40 | 0.39 |
| Weight, grams (free base) | 5.78 | 5.54 | 17.59 | 0.96 | 0.94 |
| Yield, % | 20.50 | 21.90 | 63.20 | 3.20 | 3.10 |
| Yield % (adjusted) | 20.50 | 21.90 | 51.30 | 3.20 | 3.10 |

While the conversion of HINAP is 96.8%, the yield of AHAP, i.e. 51.3% is substantially lower than the 95.1% yield obtained in Example 2. The major impurities or undesired products in Example 5 were tyramine (21.9%) and octopamine (20.5%). Thus, it can readily be seen that the use of a mixture of the liquid carboxylic acid and a dipolar aprotic solvent defeats the desired end purpose of obtaining high yields. The comparison of Example 2 with Example 5 readily exemplifies the unexpected results in the use of only the liquid carboxylic acid in the hydrogenation step.

EXAMPLE 6

Oxidation of 4-Hydroxyacetophenone with Nitrosyl Chloride in Water Followed by Amination Nitrosyl chloride is produced externally in a generator and fed into an aqueous acidic solution of the ketone in the reactor. The reaction to generate NOCl initiates the subsequent reaction with the ketone.

Generator. A 12-liter 3-neck flask to be used as a NOCl generator is charged with HCl (5663 g of 32% aqueous solution, 49.7 moles). The flask is equipped with a mechanical stirrer, liquid inlet tube adaptor and gas outlet tube adaptor. In a 2-liter erlenmeyer, NaNO$_2$, (2588 g of 42% aqueous solution, 15.8 moles) is charged. The nitrite solution is pumped into the generator flask at a rate of 21.6 g/min using a peristaltic pump.

Reactor. A 12-liter, 4-neck, jacketed flask with bottom drain valve is charged with 4-hydroxyacetophenone (4-HAP, 619 g, 4.6 moles), H$_2$O (2622 g, 145.7 moles) and HCl (887 g of a 32% aqueous solution, 7.8 moles). The flask is equipped with a mechanical stirrer (glass shaft, TFE stir paddle), gas inlet tube adaptor with subsurface sparge tube, nitrogen inlet, thermowell, and gas outlet adaptor. The reactor is connected to the generator using ¼" OD TFE tubing which is piped such that the stream of NOCl can be diverted to a scrubber which consists of a 500 ml vacuum flask with rubber stopper drilled to accommodate the ¼" tubing. Similarly, the outlet from the reactor is connected to a separate scrubber. The scrubbers are charged with 250 ml of a 20% NaOH aqueous solution. The reaction flask contents are stirred and flask is purged with nitrogen to remove residual air. The temperature of the reaction flask is set to 45° C. using a chiller/circulator. Once the NaNO$_2$ is added to the generator, the nitrogen purge is stopped and the gas bubbles in the scrubber can be observed to coincide with the rate of the NaNO$_2$ addition. By lowering the set-point of the chiller, the temperature of the exothermic reaction is maintained below 50° C. The 4-HAP is observed to go into solution when about 2/3 of the $NaNO_2$ has been added to the generator. After the addition is complete, the $NOCl$ stream is diverted to the scrubber and the nitrogen sparge is resumed in the reactor (subsurface) to remove excess $NOCl$ for thirty (30) minutes. The chiller is then set to cool the stirred reactor contents to 10° C. During this cool-down, the tancolored hydroxyphenyl glyoxal (HPGO) crystals fall out of solution. The slurry is drained and filtered through a fritted coarse Buchner to afford a tan solid (961 g, 54.6% pure, 69% isolated/84.2% total yield HPGO).

The HPGO (five grams) is then added to a 300 milliliter vessel which contains 100 ml (30% solution of 1.0 molar $NH_2OH$). After stirring for about five minutes, the precipitate is filtered through a Buchner funnel to afford a dark tan solid which analyzes by LC to be HINAP. Example 6 is generally shown by the equations in Scheme 1.

Although the invention has been illustrated by certain of the preceding examples, it is not to be construed as being limited thereby; but rather, the invention encompasses the generic area as disclosed herein. Various modifications and embodiments can be made without departing from the spirit and scope thereof.

What is claimed is:

1. The method of preparing an arylketoamine, which comprises:

(a) providing an arylalkanone compound of the formula:

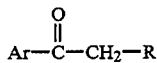

in which R represents hydrogen or a $C_1$-$C_8$ alkyl or cycloalkyl and Ar represents an aromatic phenyl radical unsubstituted, or substituted at the ortho and/or para position, or naphthyl radical unsubstituted or substituted at one or more of the 1, 3, 6, and 7 positions, wherein the substituents, one or more, are selected from the group of hydroxyl, alkoxy, alkyl, phenyl, benzyl, and aryloxy radicals, wherein the alkyl in the alkyl-containing substituent(s) is a branched or unbranched $C_1$-$C_8$ alkyl radical and any such alkyl radical as well as the phenyl and benzyl radicals may be optionally substituted with one or more substituents selected from hydroxyl, sulfonic acid, and sulfinic acid radicals, the phenyl and benzyl substituents also or alternatively being optionally substituted with one or more $C_1$-$C_8$ alkyl or $C_1$-$C_8$ alkoxy, or both, radicals, (b) reacting said arylalkanone with a lower alkyl nitrite in the presence of a strong acid and a dipolar aprotic solvent to produce a reaction mixture which includes an arylisonitrosoalkanone reaction product and water of reaction in said solvent, (c) removing water from said reaction mixture, and (d) contacting said dried reaction product with hydrogen and a liquid carboxylic acid, which is capable of substantially dissolving said reaction mixture, in the presence of a hydrogenation catalyst comprising a transition metal catalyst on an inert support.

2. The method of claim 1, wherein the amount of said transition metal present ranges from about 0.05% by weight to about 1.5% by weight of said compound of step a).

3. The method of claim 2, wherein said transition metal is selected from the group consisting of platinum, palladium, nickel, rhodium, and combinations thereof.

4. The method of claim 1, wherein said step (c) comprises evaporating said water of reaction.

5. The method of claim 1, wherein said step (c) comprises contacting said reaction mixture with a drying agent for absorbing said water of reaction.

6. The method of claim 1, wherein said step (c) comprises contacting said reaction mixture with a solid adsorbent for adsorbing said water of reaction.

7. The reaction of claim 1 in which said aryltalkanone is o- or p-hydroxyacetophenone, said strong acid in step (b) is hydrochloric acid, and said hydrogenation catalyst is palladium on a carbon support.

8. The method of claim 7 in which said solvent of step (b) is selected from dimethylsulfoxide, acetonitrile, dimethylformamide, diethylacetamide and hexamethylphosphoric acid triamide.

9. The method of claim 8 in which said palladium, exclusive of said carbon support, is present in a quantity ranging from about 0.005% by weight to about 1.5% by weight based on the weight of said o- or p-hydroxyacetophenone, and wherein said step (d) reaction is conducted under hydrogen pressure ranging from about 1.0 psi to about 300 psi at temperatures in the range of from about 10° C. to about 35° C., and the liquid carboxylic acid is acetic acid.

* * * * *